United States Patent [19]

Gugliotta

[11] 4,099,051
[45] Jul. 4, 1978

[54] INSPECTION APPARATUS EMPLOYING A CIRCULAR SCAN

[75] Inventor: George Gugliotta, Ridgefield, Conn.

[73] Assignee: Automation Systems, Inc., Brookfield, Conn.

[21] Appl. No.: 742,918

[22] Filed: Nov. 18, 1976

[51] Int. Cl.² ................ G01N 21/32; G01N 21/48
[52] U.S. Cl. ......................... 250/236; 250/223 R; 356/210; 356/237
[58] Field of Search ............... 250/223 R, 223 B, 236, 250/567; 356/237, 210

[56] References Cited

U.S. PATENT DOCUMENTS

| | | | |
|---|---|---|---|
| 3,072,798 | 1/1963 | Sick | 250/236 X |
| 3,150,266 | 9/1964 | Mathias | 250/223 B |
| 3,790,287 | 2/1974 | Cuthbert et al. | 356/237 X |
| 3,899,687 | 8/1975 | Jones | 250/223 X |
| 3,976,384 | 8/1976 | Matthews et al. | 356/237 X |

*Primary Examiner*—Palmer C. Demeo
*Attorney, Agent, or Firm*—Martin Novack

[57] ABSTRACT

The disclosure is directed to an apparatus for inspecting the surface of an object at an inspection position. In accordance with an embodiment of the invention, source means are provided for generating a relatively narrow collimated beam of radiation, the source preferably, but not necessarily, being a laser. A scanning means, spaced from the inspection position, is provided for effecting a substantially circularly shaped scan of the laser beam at the inspection position. The scanning means may typically comprise a tilted rotatable mirror which is rotated at the scan rate. A reflector means is disposed between the scanning means and the inspection position. The reflector means, typcially a mirror, has an aperture therein to allow passage of the scanning beam travelling toward the inspection position. The mirror reflective surface is oriented angularly with respect to the axis of the scan so that radiation received from the object is reflected toward an off-axis region. Photodetector means are located at the off-axis region, and a lens means, disposed between the reflector means and the photodetector, serves to focus radiation from the reflector means onto the photodetector. In a preferred embodiment of the invention, a second reflective surface is mounted on the rear of the reflector means. The source means is adapted to direct the beam toward the second reflective surface which is oriented to reflect the beam toward the tilted rotatable mirror. In one form of this embodiment, the second reflective surface is a corner mirror mounted adjacent the aperture. In another form of this embodiment, the second reflective surface is mounted centrally within the aperture. In another embodiment of the invention, a second lens means is disposed between the inspection position and the reflector means to focus energy from the object onto the reflector means.

17 Claims, 5 Drawing Figures

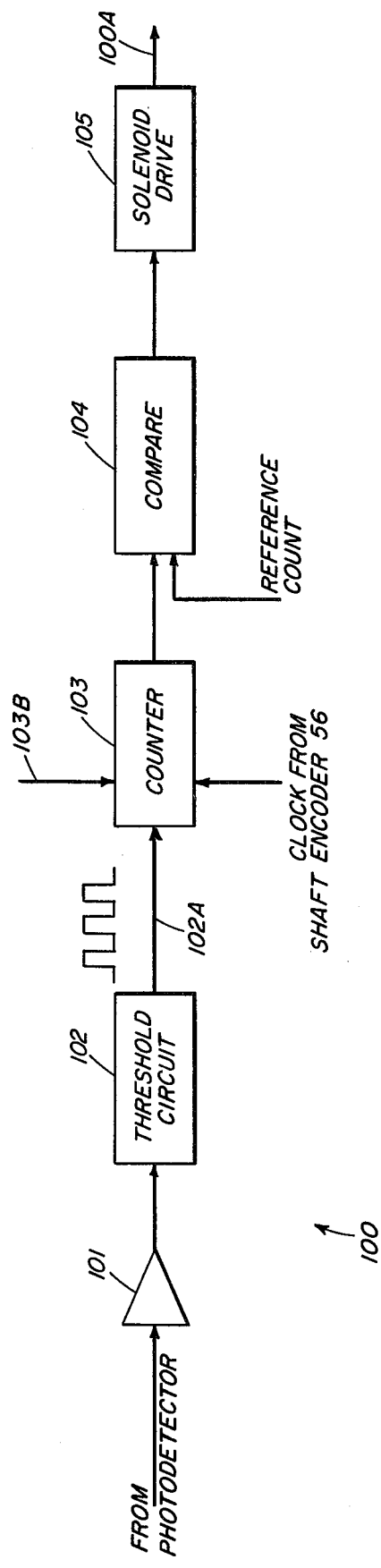

INSPECTION APPARATUS EMPLOYING A CIRCULAR SCAN

BACKGROUND OF THE INVENTION

This invention relates to the field of automatic inspection and, more particularly, to an apparatus for inspecting the surface of an object using a beam of radiation, such as a laser beam.

The automatic inspection of parts with a laser beam is gaining widespread commercial acceptance. For example, in my U.S. Pat. Nos. 3,816,746 and 3,983,388, assigned to the same assignee as the present application, there are disclosed apparatus for automatically inspecting hardware items by scanning a laser beam over a threaded surface of a hardware item at an inspection position and then detecting the nature of the reflected energy to determine the presence of defects or count threads, etc. Various other systems are also available for scanning surfaces with a laser beam and determining the properties of the surface by detecting the characteristics of the laser light reflected from the surfaces. In general, the scan of the inspecting beam is linear in nature, usually being either a line scan or a field scan made up of line scans. These types of scans are suitable for inspecting many types of surfaces and, for some applications, they can be generated and tracked for detection without undue system complexity.

Many objects, for example gears, bearing races, and tampon ends, are not conveniently inspected using a linear scan since they have generally circular surface or circular symmetry which would be more efficiently inspected using a substantially circular scan. Techniques for obtaining a circular scan of a light beam are known in the art. However, there are problems associated with generating such a beam for inspection purposes, and then collecting the radiation reflected off the inspected object's surface. For example, it is necessary that the collecting optics not interfere with the scanning beam, while maintaining the collection efficiency as high as possible. Also, the optical system should ideally be kept as simple as possible to minimize cost. Further, the need for expensive detector arrays, which introduce unreliability and expense, should be avoided, if possible.

It is one object of the present invention to provide an apparatus for inspecting the surface of objects with a substantially circular scan, the apparatus operating at relatively high efficiency with a minimum of parts and requiring only a simple detector.

SUMMARY OF THE INVENTION

The present invention is directed to an apparatus for inspecting the surface of an object at an inspection position. In accordance with an embodiment of the invention, source means are provided for generating a relatively narrow collimated beam of radiation, the source preferably, but not necessarily, being a laser. A scanning means, spaced from the inspection position, is provided for effecting a substantially circularly shaped scan of the laser beam at the inspection position. The scanning means may typically comprise a tilted rotatable mirror which is rotated at the scan rate. A reflector means is disposed between the scanning means and the inspection position. The reflector means, typically a mirror, has an aperture therein to allow passage of the scanning beam travelling toward the inspection position. The mirror reflective surface is oriented angularly with respect to the axis of the scan so that radiation received from the object is reflected toward an off-axis region. Photodetector means are located at the off-axis region, and a lens means, disposed between the reflector means and the photodetector, serves to focus radiation from the reflector means onto the photodetector.

In a preferred embodiment of the invention, a second reflective surface is mounted on the rear of the reflector means. The source means is adapted to direct the beam toward the second reflective surface which is oriented to reflect the beam toward the tilted rotatable mirror. In one form of this embodiment, the second reflective surface is mounted centrally within the aperture. In another embodiment of the invention, a second lens means is disposed between the inspection position and the reflector means to focus energy from the object onto the reflector means.

Further features and advantages of the invention will become more readily apparent from the following detailed description when taken in conjunction with the accompanying drawings.

BRIEF DESCRIPTION OF THE DRAWINGS

FIG. 5 is a block diagram of an embodiment of the detection circuitry 100 of FIG. 1.

DESCRIPTION OF THE PREFERRED EMBODIMENT

Figure 1:
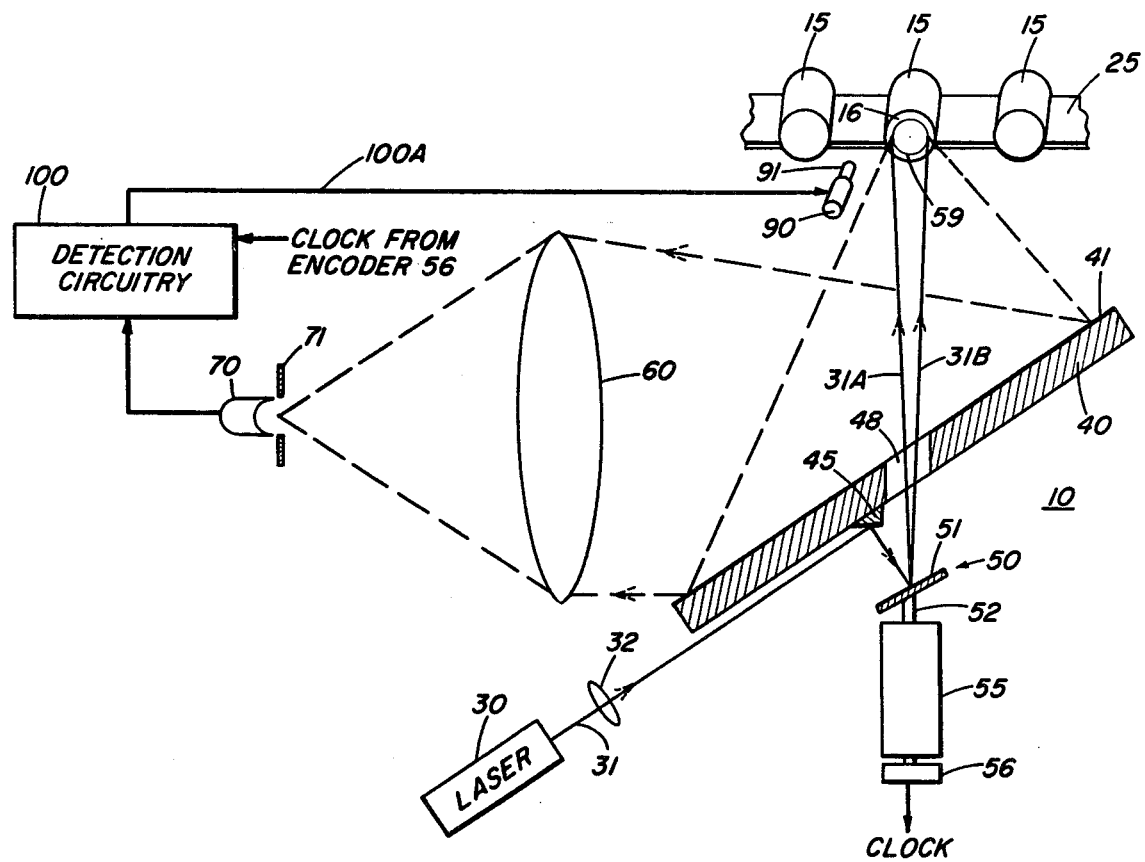
FIG. 1 is a schematic diagram, partially in block form, of an apparatus in accordance with an embodiment of the invention.

Referring to FIG. 1, there is shown an embodiment of an apparatus 10 for inspecting an end surface 16 of generally cylindrical object 15 at an inspection position 20. The objects 15 progresses along a track or belt 25, and the presence of a new object at the inspection position can be sensed by any suitable means, such as is described in the above-referenced U.S. Pat. No. 3,816,746.

A laser 30 generates a beam of laser radiation, represented in the FIG. by the line 31, which is focused by a lens 32 and directed by a corner mirror 45 toward a scanner 50. In the present embodiment the scanner 50 comprises tilted mirror 51 mounted on the shaft 52 of a motor 55. A shaft encoder 56 generates clock signals which relate to the angular rotation of the mirror 51. The mirror is tilted with respect to the shaft, and the beam 31 incident thereon is caused to scan in a substantially circular pattern at the inspection position, as depicted by the circular line 59. The lines 31A and 31B depict the beam at two diametrically opposing positions during the scan. Laser light returning from the surface 16, which may be either a good or poor reflector or disperse the light to some degree, is reflected by a relatively large mirror 40 toward a receiving lens 60. Mirror surface 41 is preferably relatively large so as to effectively collect light which may be dispersed over a relatively large solid angle. The mirror 40 has an aperture 48 therein for passage of the scanning beam. Light reflected from the surface 41 of mirror 40 is collected by a receiving lens 60 and focused at a photodetector 70. A stop 71 minimizes the effect of stray radiation.

The output of photodetector 70 is coupled to detection circuitry 100 which also receives the clock signals from shaft encoder 56. Detection circuitry 100 detects prescribed conditions of the photodetector output and generates an acceptance or rejection signal on a line 100A which controls a solenoid 90 disposed along the track 25. Solenoid 90 has a plunger 91 which, when activated, serves to deflect rejected objects 15 off the track 25. It will be understood, however, that the invention is not limited to any particular detection circuitry 100 or activating means, these items being generally known in the art and disclosed, for example, in the U.S. Pat. Nos. 3,816,746 and 3,983,388. By providing the circular scan through the aperture 48 in the relatively large mirror 40, collection of the light emanating from the object is efficiently achieved without the need for cumbersome and complex optics.

Figure 2:
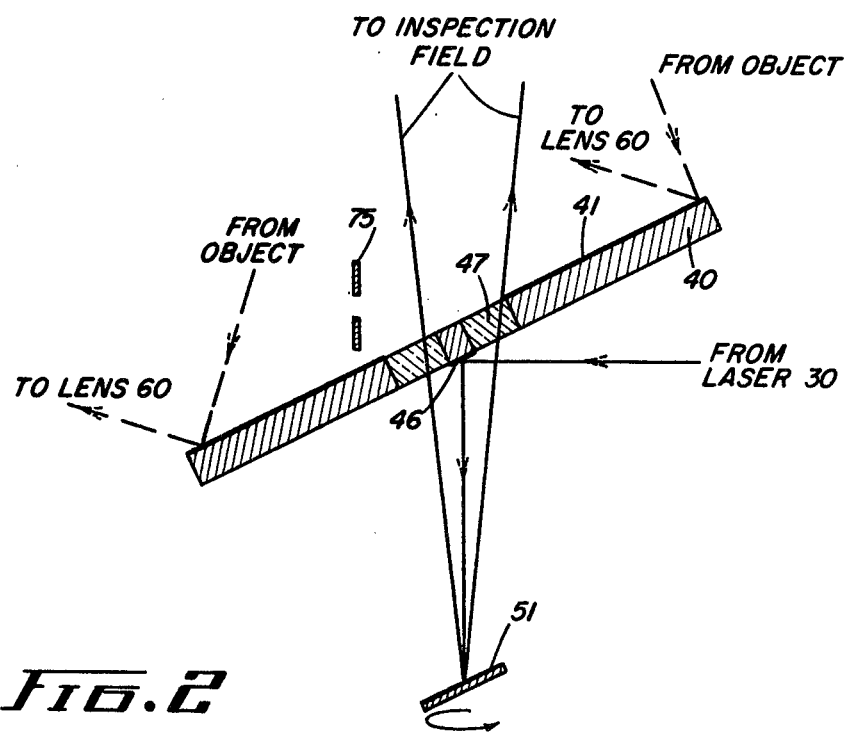
FIG. 2 illustrates a variation of the apparatus of FIG. 1, in accordance with another embodiment of the invention.

Referring to FIG. 2, there is shown another embodiment of the invention wherein the corner mirror 45 is replaced by a flat mirror segment 46 which is centrally mounted in the aperture 48 in mirror 40. The mirror segment 46 is mounted on a transparent glass disk 47 which passes the beam for an essentially perfectly circular scan. The stop 75 blocks undesired reflection from the glass disk 47.

Figure 3:
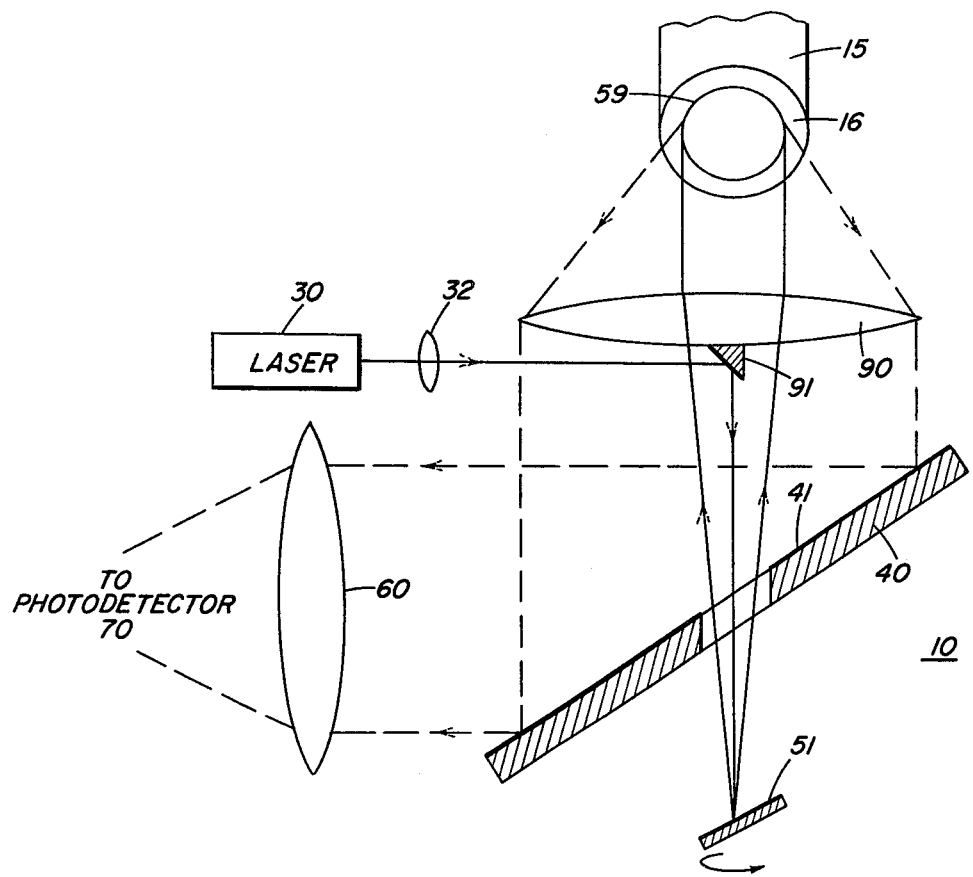
FIG. 3 illustrates a further variation of the apparatus of FIG. 1, in accordance with another embodiment of the invention.

FIG. 3 ilustrates a still further embodiment of the invention wherein there is provided an additional lens 90 which reflects light imaged from the object and directs it toward the mirror 40. In this embodiment, the incident laser beam is directed toward a corner mirror 91 which is centrally mounted on the lens 90.

Figure 4:
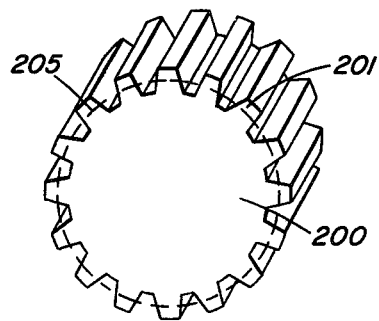
FIG. 4 illustrates a gear wheel and circular scan of the teeth of said gear wheel.

FIG. 4 illustrates a type of automatic inspection wherein the apparatus of FIGS. 1-3 can be advantageously employed. The gear wheel 200 has teeth 201 which are suitable for inspection using the circular scan 205 shown in dashed line. An example of a detection circuitry 100 (FIG. 1) for this application is shown in FIG. 5. The signal from photodetector 70 is coupled via preamp 101 to threshold circuit 102 which, in the present example, will produce a pulse train that is determined by the presence of the gear teeth 201 during the circular scan. The pulse train, on a line 102A, is one input to a counter 103. The counter also receives the clock signal from shaft encoder 56 (FIG. 1). The clock signals from the shaft encoder provide one count each time the scanner traverses a predetermined angular rotation, for example one degree. Counter 103 is adapted to be reset by the pulses on line 102A. A further signal on a line 103B sets the counter each time a part enters the inspection field. In operation, each time a gear tooth is encountered, the pulses on line 102A reset the counter to zero. If a tooth is missing, the counter will accumulate an excessive count which is detected by a comparator 104 which receives, as its other input, a reference count. The output of comparator 104 is coupled to a solenoid drive 105 which produces the signal on line 100A (FIG. 1) which activates the plunger 91 of solenoid 90. In a similar manner, an unduly low count, indicative of excess metal due to die failure or the like, could be detected by another comparator (not shown) to generate a signal indicative of this different type of failure.

The invention has been described with reference to particular embodiments, but variations within the spirit and scope of the invention will occur to those skilled in the art. For example, it will be understood that reference to a substantially circular scan is intended to generically include scans which are essentially circular and to include, for instance, elliptical scans on this nature. Also, the particular type of detection circuitry utilized will depend upon the type of objects being inspected and modes of failure expected to be encountered. For example, localized surface irregularities such as burrs, pits or scratches can be determined by examination of the optical data generated with reference to a self-adjusting time scale. This can be done by detection of "data clusters" that would be characteristic of scratches or pits that occur during only a relatively small portion of total scan time.

I claim:
1. Apparatus for inspecting the surface of an object at an inspection position, comprising:
    a. source means for generating a relatively narrow collimated beam of radiation;
    b. scanning means, spaced from the inspection position, for effecting a substantially circularly shaped scan of said beam at the inspection position;
    c. reflector means, disposed between said scanning means and the inspection position, said reflector means having an aperture therein to allow passage of the scanning beam travelling toward the inspection position and having its reflective surface oriented angularly with respect to the axis of said scan so as to receive radiation from said object and reflect it toward an off-axis region;
    d. photodetector means located at said off-axis region; and
    e. lens means disposed between said reflector means and said photodetector means for focusing radiation on said photodetector means.

2. Apparatus as defined by claim 1 wherein said source means comprises a source of laser light.

3. Apparatus as defined by claim 2 further comprising second lens means disposed between the inspection position and said reflector means to focus energy from said object onto said reflector means.

4. Apparatus as defined by claim 2 wherein said scanning means comprises a tilted rotatable mirror.

5. Apparatus as defined by claim 3 wherein said scanning means comprises a tilted rotatable mirror.

6. Apparatus as defined by claim 4 further comprising a second reflective surface mounted on the rear of said reflector means; and wherein said source means is adapted to direct the beam toward said second reflective surface, said second reflective surface being oriented to reflect the beam toward said tilted rotatable mirror.

7. Apparatus as defined by claim 5 further comprising a second reflective surface mounted on the rear of said reflector means; and wherein said source means is adapted to direct the beam toward said second reflective surface, said second reflective surface being oriented to reflect the beam toward said tilted rotatable mirror.

8. Apparatus as defined by claim 6 wherein said second reflective surface is mounted centrally within said aperture.

9. Apparatus as defined by claim 7 wherein said second reflective surface is mounted centrally within said aperture.

10. Apparatus as defined by claim 6 wherein said second reflective surface is mounted adjacent said aperture.

11. Apparatus as defined by claim 7 wherein said second reflective surface is mounted adjacent said aperture.

12. Apparatus as defined by claim 2 further comprising detection means coupled to said photodetector for generating an occurrence indication when a predetermined characteristic is detected in the photodetector output.

13. Apparatus as defined by claim 5 further comprising detection means coupled to said photodetector for generating an occurrence indication when a predetermined characteristic is detected in the photodetector output.

14. Apparatus as defined by claim 7 further comprising detection means coupled to said photodetector for generating an occurrence indication when a predetermined characteristic is detected in the photodetector output.

15. Apparatus as defined by claim 9 further comprising detection means coupled to said photodetector for generating an occurrence indication when a predetermined characteristic is detected in the photodetector output.

16. Apparatus as defined by claim 5 further comprising a second reflective surface mounted on said second lens means; and wherein said source means is adapted to direct the beam toward said second reflective surface, said second reflective surface being oriented to reflect the beam toward said tilted rotatable mirror.

17. Apparatus as defined by claim 16 wherein said second reflective surface is centrally mounted on said second lens means.

* * * * *